(12) United States Patent
Goldstein

(10) Patent No.: US 11,937,719 B2
(45) Date of Patent: Mar. 26, 2024

(54) ORAL HYDRATION APPARATUS

(71) Applicant: Loren Goldstein, Chicago, IL (US)

(72) Inventor: Loren Goldstein, Chicago, IL (US)

( * ) Notice: Subject to any disclaimer, the term of this patent is extended or adjusted under 35 U.S.C. 154(b) by 1241 days.

(21) Appl. No.: 16/016,001

(22) Filed: Jun. 22, 2018

(65) Prior Publication Data

US 2018/0368598 A1 Dec. 27, 2018

Related U.S. Application Data

(60) Provisional application No. 62/524,268, filed on Jun. 23, 2017.

(51) Int. Cl.
| | | |
|---|---|---|
| *A47G 21/18* | (2006.01) | |
| *A61M 3/02* | (2006.01) | |
| *A45F 3/16* | (2006.01) | |
| *A61C 17/02* | (2006.01) | |
| *A61J 15/00* | (2006.01) | |

(52) U.S. Cl.
CPC ............. *A47G 21/185* (2013.01); *A61M 3/02* (2013.01); *A61M 3/0208* (2014.02); *A61M 3/022* (2014.02); *A61M 3/0279* (2013.01); *A45F 3/16* (2013.01); *A61C 17/0211* (2013.01); *A61J 15/0011* (2013.01); *A61J 15/0084* (2015.05); *A61J 15/0088* (2015.05); *A61M 2210/0637* (2013.01)

(58) Field of Classification Search
CPC ................ A61J 15/0011; A61J 15/0084; A61J 15/0088; A61J 7/0061; A61J 15/001; A61M 2210/0637; A61M 2210/0625; A61M 16/049; A61M 16/0488; A47G 21/185
See application file for complete search history.

(56) References Cited

U.S. PATENT DOCUMENTS

| | | | |
|---|---|---|---|
| 3,939,875 | A | 2/1976 | Osborn et al. |
| 4,106,501 | A * | 8/1978 | Ozbey ............... A61C 17/0211 |
| | | | 433/80 |
| 4,838,882 | A | 6/1989 | Molinoff |
| 6,413,238 | B1 | 7/2002 | Maget |
| 6,893,259 | B1 * | 5/2005 | Reizenson ......... A61C 17/0211 |
| | | | 433/29 |
| 7,438,711 | B2 | 10/2008 | Deniega et al. |
| 7,571,727 | B2 | 8/2009 | Croll |
| 8,372,020 | B2 | 2/2013 | Martin et al. |
| 8,771,149 | B2 | 7/2014 | Rahman et al. |

(Continued)

OTHER PUBLICATIONS

United States Patent and Trademark Office, Notification of Transmittal of the International Search Report and the Written Opinion of the International Search Authority, or the Declaration for International Application No. PCT/US2018/039056 (dated Sep. 19, 2018).

(Continued)

*Primary Examiner* — Tiffany Legette

(74) *Attorney, Agent, or Firm* — Neal, Gerber & Eisenberg LLP

(57) ABSTRACT

Systems, devices, and methods are disclosed for maintaining oral hydration. A device may include a perforated tube, covered by an outer cover made of an absorbent material. The tube may be shaped such that it allows a patient using the device to open and close his or her jaw, without displacement and also to allow other medical devices to be used on the patient simultaneously.

20 Claims, 4 Drawing Sheets

(56) References Cited

U.S. PATENT DOCUMENTS

| | | | |
|---|---|---|---|
| 2006/0149192 A1* | 7/2006 | Deniega | A61M 25/007 604/264 |
| 2010/0016908 A1* | 1/2010 | Martin | A61M 16/049 607/3 |
| 2011/0220124 A1* | 9/2011 | Vaska | A61M 1/63 128/848 |
| 2013/0025607 A1 | 1/2013 | Altounian | |
| 2014/0371643 A1 | 12/2014 | Martin et al. | |
| 2017/0151404 A1* | 6/2017 | Hunt | A61M 39/10 |
| 2018/0312326 A1* | 11/2018 | Haden | A61G 7/0503 |

OTHER PUBLICATIONS

Office Action dated Sep. 6, 2003 for Canadian Patent Application 3,067,638.

* cited by examiner

ORAL HYDRATION APPARATUS

PRIORITY CLAIM

This patent application claims priority to U.S. Provisional Patent Application No. 62/524,268, which was filed Jun. 23, 2017, the entire contents of which are herein incorporated by reference.

TECHNICAL FIELD

The present disclosure generally relates to the field of oral devices and, more particularly, devices and systems that enable a patient to alleviate mouth dryness and maintain oral and systemic hydration.

BACKGROUND

Modern medical procedures can take place over long periods of time, and without proper hydration can cause a patient's mouth to dry out. In addition to dental procedures, many other activities and aspects of daily life can be improved by having and maintaining proper dental hydration.

Some techniques to solve the issue of mouth dryness can include pills or other mints or rinses (which can have limited effectiveness) and complex and obtrusive devices. These devices may not be convenient and may cause discomfort to patients, and are not effective at night or on compromised patients.

BRIEF DESCRIPTION OF THE DRAWINGS

For a better understanding of the invention, reference may be made to embodiments shown in the following drawings. The components in the drawings are not necessarily to scale and related elements may be omitted, or in some instances proportions may have been exaggerated, so as to emphasize and clearly illustrate the novel features described herein. In addition, system components can be variously arranged, as known in the art. Further, in the drawings, like reference numerals designate corresponding parts throughout the several views.

SUMMARY

Figure 1A:
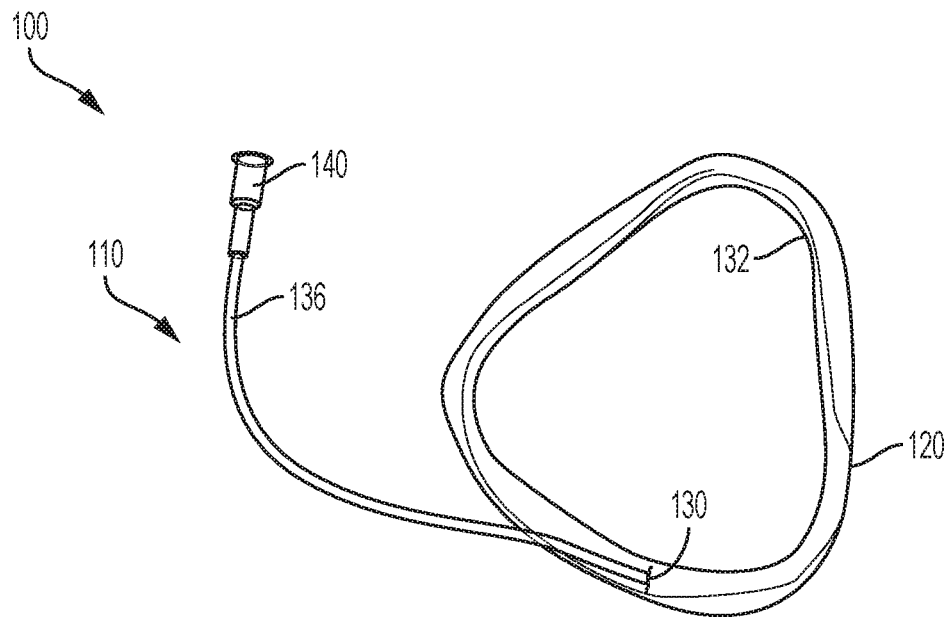
FIGS. 1A and 1B illustrate overhead perspective views of an example apparatus according to embodiments of the present disclosure.

The appended claims define this application. The present disclosure summarizes aspects of the embodiments and should not be used to limit the claims. Other implementations are contemplated in accordance with the techniques described herein, as will be apparent to one having ordinary skill in the art upon examination of the following drawings and detailed description, and these implementations are intended to be within the scope of this application.

Example embodiments are shown describing systems, apparatuses, and methods for maintaining adequate oral hydration. An example device includes a flexible tube comprising a first end and a second end, wherein the flexible tube is configured to conform to the contours of a patient's mouth. The device also includes a plurality of holes defined by the flexible tube, positioned along a length of the flexible tube between the first end and the second end. And the device further includes a flexible cover configured to encapsulate the flexible tube.

Another example device includes a flexible tube comprising a first end and a second end, wherein the flexible tube is configured to conform to the contours of a patient's mouth, and wherein the flexible tube is formed from a porous material, and a flexible cover configured to encapsulate the flexible tube.

An example method of using an oral hydration device includes inserting a device into a patient's mouth, the device comprising a flexible tube comprising a first end and a second end, wherein the flexible tube is configured to conform to the contours of the patient's mouth, a plurality of holes defined by the flexible tube, positioned along a length of the flexible tube between the first end and the second end, and a flexible cover configured to encapsulate the flexible tube. The method also includes coupling the first end of the device to a fluid source. And the method further includes dispersing fluid from the fluid source into the patient's mouth through one or more of the plurality of holes.

DETAILED DESCRIPTION OF EXAMPLE EMBODIMENTS

While the invention may be embodied in various forms, there are shown in the drawings, and will hereinafter be described, some exemplary and non-limiting embodiments, with the understanding that the present disclosure is to be considered an exemplification of the invention and is not intended to limit the invention to the specific embodiments illustrated.

As noted above, mouth dryness can be an issue in many contexts. These may include medical contexts, such as a patient in a coma or under general anesthesia, patients taking any of more than 300 drugs that have mouth dryness as a side effect, patients requiring the use of a CPAP machine, people who snore, and people wearing appliances for the treatment of temporomandibular joint and muscle disorders (TMJ disorders). Further, people may experience mouth dryness during physical activities, such as while working out or participating in sports or other physical activities requiring hydration without interruption of the activity.

Conventional solutions to mouth dryness may include lozenges, mouth rinses, and drugs. However these solutions are not always effective. Many of these solutions require the patient to be awake, and do not provide a lasting benefit. Further, these solutions are patient dependent, meaning that a patient's natural salivary function will impact the effectiveness of the attempted solution. Further, the ingestion of some drugs for the purpose of alleviating mouth dryness can become complicated when the source of the mouth dryness is another drug taken by the patient, to treat an underlying condition.

As such, there is a need for a simplified, streamlined, and unobtrusive device or system that can provide adequate externally supplied oral hydration.

In some aspects, a system for delivery of liquid to a mouth of a user is provided. The system may include a pump including a housing, a bladder supported by and within the housing, an inlet in fluid communication with the bladder, and an outlet in fluid communication with the bladder, a tube having a first end and a second end, the first end of the tube being coupled to the outlet of the elastomeric pump, and an oral device positionable in a mouth of a user and including a coupler, the second end of the tube being coupled to the coupler. In some aspects, the systems and devices described herein may be used for treating one or more illnesses or conditions such as Xerostomia, or other conditions of systemic dehydration, and more. Further, the systems and devices disclosed herein may be used in connection with general surgery or procedures, to ensure that adequate moisture is maintained in the mouth and throat tissues Example embodiments disclosed herein may include a slender and unobtrusive perforated tube that can be placed inside a patient's mouth, in order to provide hydration directly to the patient's mouth. Example embodiments may further provide devices that maintain their position within the patient's mouth without requiring additional components to affix the device to the patient's teeth (such as clips, prongs, or other members). Devices described herein may be configured such that the patient's jaw and teeth can move freely without dislodging the device, enabling a patient to talk and function normally even while using the device.

The devices disclosed herein may be compatible with a number of other medical devices, such as CPAP machines, sleep apnea devices, snore reduction devices, TMJ appliances, and the like. Further, the devices disclosed herein may also be compatible with dentures and edentulous patients, coma patients, and anesthetized patients. As such, the devices may be compatible and can be used alongside intubation tubes, nasal cannulas, and other devices used in medical and non-medical contexts.

Devices disclosed herein may be particularly useful where a patient has no or reduced salivary function, is dehydrated and requires an external supplementation of fluids, and where other medical or oral/dental procedures are used simultaneously.

Figure 1B:
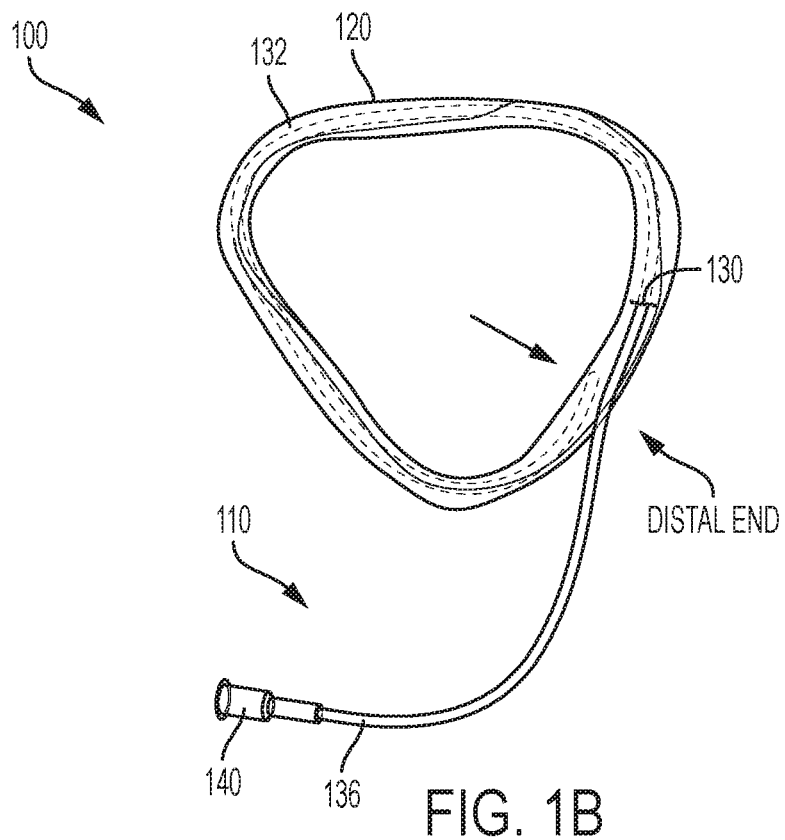

FIGS. 1A and 1B illustrate respective views of a device 100 of the present disclosure. Device 100 may include a tube 110 having one or more small holes or perforations, configured to allow liquid inside the tube to be dispersed slowly and evenly through the tube. The perforations or holes may be only present on a segment of the tube 110, such as a segment that is configured to rest inside a patient's mouth and/or inside the outermost borders of the cheeks (the Buccal Mucogingival Folds). The tube 110 may be configured such that it follows the contour of the mouth of a patient, and curves on the sides of the mouth to allow the patient's jaw to open and close without restriction. Further, the tube 110 may include a protruding segment 136 that does not include any perforations or holes, which may be referred to as the "feeder line." The protruding segment 136 may enable liquid to be pumped or pushed into the inner mouth section for dispersal onto the patient's mouth.

In some examples, the holes may be evenly spaced along the tube 110, while in other examples the holes may not be evenly spaced. Further, the holes may be positioned along the tube around the circumference of the tube in the same plane, or along a plurality of different planes. The holes may have any geometry, pattern, or orientation.

In some examples, the holes may all be the same size, while in other examples, the holes may have different sizes. For instance, the holes may be smaller near a first end of the inner mouth portion 132, and be larger toward a second end of the inner mouth portion 132. In this way, fluid may be evenly distributed into the user's mouth. Further, the holes may be larger or smaller on the portion of tube 110 that is proximate the back of the user's mouth as compared to the portion of the tube that is proximate the front.

It should be understood that the various hole sizes, arrangements, orientations, and other examples are disclosed herein for exemplary purposes only, and that any other number, arrangement, size, or orientation of holes may be used.

The inner mouth portion 132 of the tube 110 may be positioned on the top set of teeth, bottom set of teeth, or both. The holes on the inner mouth portion may be located on only a portion, such that the holes are only on the top part, only on the bottom part, entirely on the left side, entirely on the right side, partially on a left side and partially on a right side, partially on the top and bottom parts, or any other combination, arrangement, or orientation.

In some examples, the holes may only be positioned on the inner mouth portion 132 of the tube 110. The inner mouth section 132 may be separated from the feeder tube 136 at point 130. Inner mouth portion 132 may have a first end coupled to point 130, and a second end that also coupled to the point after looping around. The second end may be capped, fused, or melted closed, such that fluid does not recirculate in the inner mouth portion 132 or back into the feeder tube 136—thereby preventing contamination of the fluid source.

In some examples, the inner mouth portion 132 may be porous, such that there are not any defined holes. Rather, the entire tube portion that rests inside the user's mouth may be porous and allow fluid to enter the user's mouth cavity.

Tube 110 may be made of plastic, or another material, and may be configured to maintain generally the shape shown in FIGS. 1 and 2. Tube 110 may be made from any material, including but not limited to soft atraumatic material such as dental grade silicone or polyvinyl siloxane, more rigid materials like dental acrylic, or a combination of soft and rigid materials. In the examples shown in the figures, the tube 110 may be made from plastic, however it should be noted that this is only an example material, and that any other suitable material may be used.

The tube 110 may be "springy" or may be configured to maintain a desired shape such that a patient can open and close his or her mouth while the tube retains its general shape and position without supplemental fixation and matches the movement of the patient's jaw. As such, the tube 110 may be configured to conform to the user's teeth and/or jaw shape.

Figure 2A:
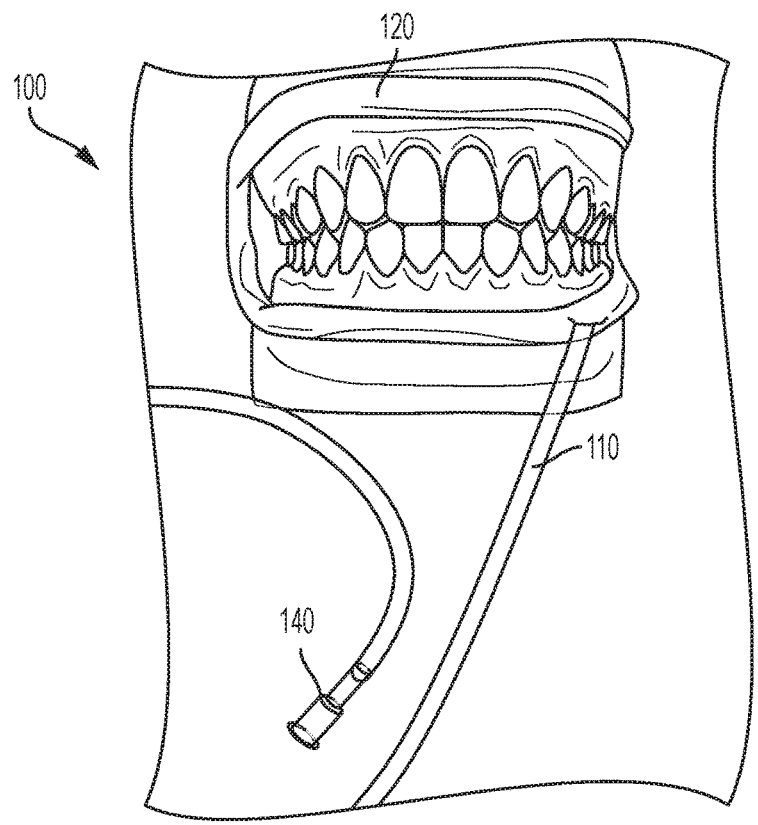
FIGS. 2A and 2B illustrate front and side perspective views of an example apparatus according to embodiments of the present disclosure.
Figure 2B:
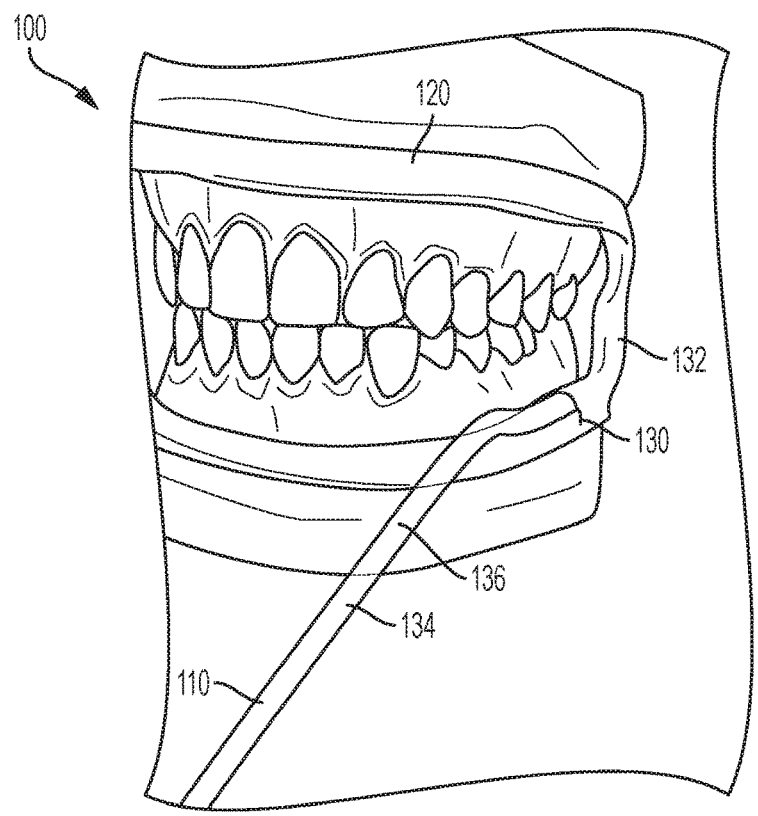

In some examples, the tube 110 may be maintained in place in the user's mouth via friction with the user's gums, cheeks, lips, and other parts of the user's mouth. Further, the springy nature of the tube 110 may be configured to bias the tube toward staying in the user's mouth and to maintain its position without falling out. This may be done by the tube pressing against and resting at the top (or bottom) of the respective oral vestibules. When the tube is placed in a patient's mouth as shown in FIGS. 2A and 2B, the nature of the tube material may cause the tube to attempt to revert back to a ring (rather than remain deformed), which pushes the top up and the bottom down causing the tube to be pushed into the buccal mucogingival folds.

The tube length may be any suitable length such that the inner mouth portion 132 can loop around either or both of the bottom and lower set of the user's teeth. As such, the inner mouth portion 132 may be 10 cm or smaller, and up to 50 cm or larger. Further, the tube diameter may be 0.1 cm or smaller, up to 1 cm or larger. Further, the size of the tube may change across the length of the tube, such that a first end of the tube has a smaller or larger diameter than a second end of the tube. Further, in some examples the tube may have a varying diameter along the length, such that the diameter increases and decreases at various positions. These are described for exemplary purposes only, and it should be understood that any tube diameter, length, and variation along the length of the tube may be used.

In some examples, the inner mouth portion 132 may be a cylindrical tube, while in other examples it may be some other shape. Further, in some examples, the tube 110 and/or inner mouth portion 132 may be tapered, such that it is larger or smaller proximate a first end than proximate a second end. Further, the inner mouth portion 132 may have one or more segments that are bigger or smaller than other segments. For instance, the tube may bulge or increase in size at various locations along the length, particularly where a hole or perforation is present. Further, in some examples the inner mouth portion 132 may be thicker in some areas than in other areas, or may be made of a more rigid material in some areas than in other areas. It may be particularly useful to have a thicker or more rigid material used for segments of the inner mouth portion 132 proximate the rear of the mouth when in use, such that crimping of the tube is prevented or reduced.

Device 100 may also include an outer cover 120 covering a portion of the tube 110. FIGS. 1A and 1B illustrate an outer cover 120 covering the inner mouth section 132 of the tube 110. This outer cover may provide comfort to a patient using device 100, as well as to allow the dispersed liquid to be retained against the patient's oral tissues. The outer cover may be absorbent or semi-absorbent, to allow the liquid dispersed through tube 110 to be absorbed and slowly dispersed onto the patient's tissues over time. The outer cover may be a fabric or other soft material, such as cotton, linen, nylon, or another type of cloth. Alternatively, the outer cover 120 may be foam, plastic, or a composite material. In some examples, the cover 120 may be braided, which may aid in the dispersal of fluid. Other materials are possible as well. The cover 120 may assist in maintaining the device within the mouth cavity of the user.

In some examples, the device may include a wear indicator, or color change indicator, to indicate when the device has expired or is approaching expiration. The fabric may include a colorant dye or other material that changes color over time to indicate when the device needs to be replaced.

FIGS. 2A and 2B illustrate front and side perspective views of device 100 according to some embodiments. FIG. 2B shows a connection point 130 between the inner mouth portion 132 and the feeder tube 136 of the tube 110.

One end of the feeder tube 136 (which may have any of several different lengths) may be coupled to a connector 140. The connector 140 may allow a user to easily change a fluid source, while retaining the inner portion 132 in his or her mouth. The connector 140 may include a mechanism that allows a patient or user to control a rate of flow of liquid into the inner mouth portion 132. In some examples, the connector 140 may be a leuer connector.

The connector 140 may be configured to disconnect the feeder tube 136 and inner mouth portion 132 from a fluid source. This can enable a user to quickly disconnect and switch out a fluid source without having to remove the inner mouth portion 132. Connector 140 may be adjacent and/or exterior to the user's oral cavity when in use. That is, the connector 140 is typically close to the patient's lips, and may be inside or outside of the patient's lips when the device is used. The connector 140 inlet may be centered at the anterior (front) portion of the device, or may be offset to the left or right side. In some examples, the device may have more than one connector.

In some examples, an axis of rotation is at a rear of the patient's mouth when the device is in use, which allows for opening and closing of the patient's jaw without displacement of the device within the patient's mouth.

Figure 3:
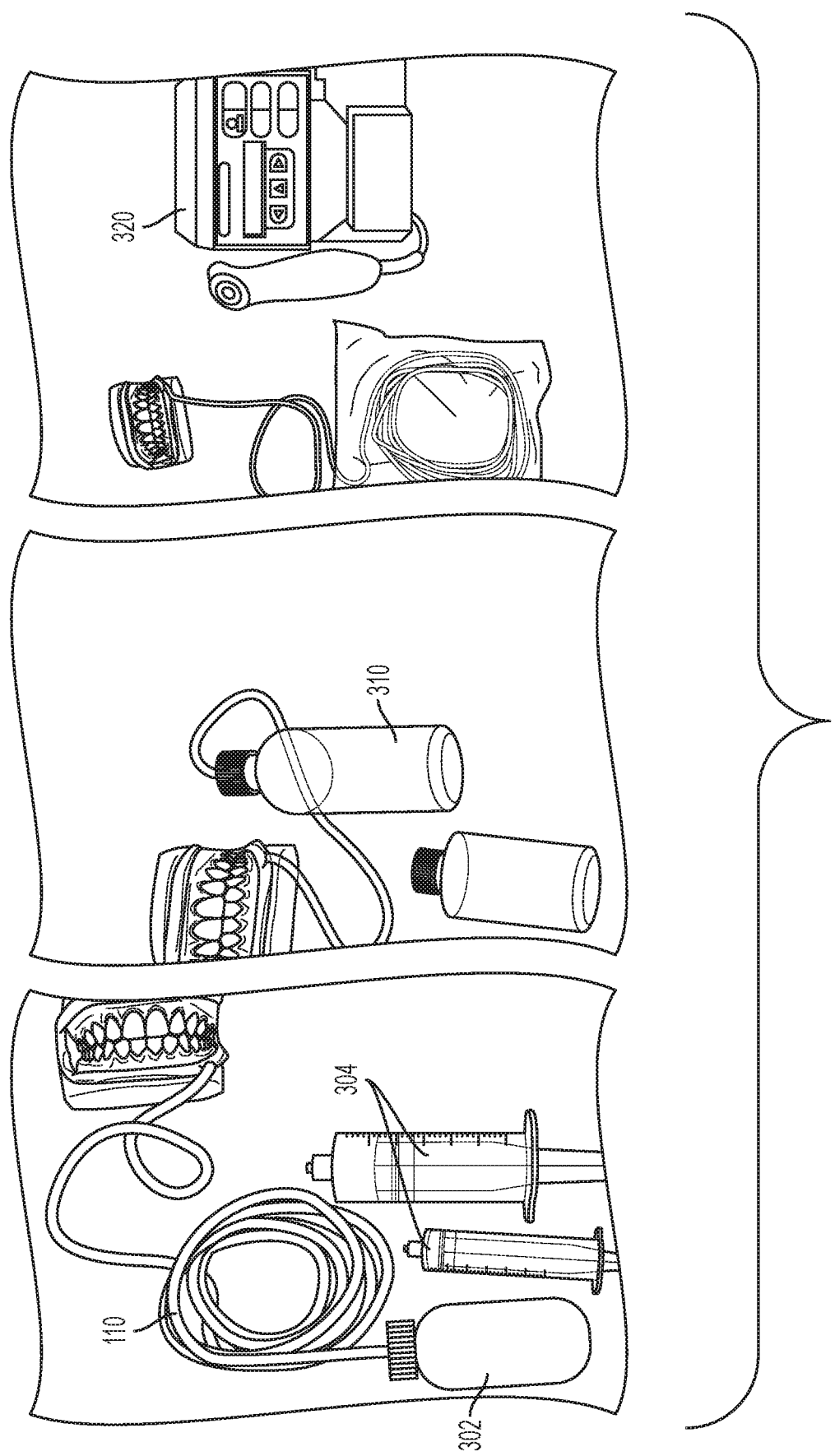
FIG. 3 illustrates example distribution mechanisms of the example apparatus of FIG. 1.
Figure 4:
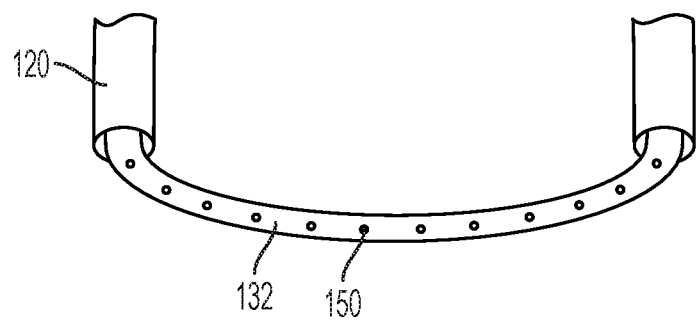
FIG. 4 illustrates a cross-section view of the flexible tube and cover according to embodiments of the present disclosure.

FIG. 3 illustrates several mechanisms that may be used to disperse liquid into the patient's mouth through the tube 110. The left-most portion of FIG. 3 shows a squeeze bottle 302 that can be coupled to the end of tube 110. The bottle 302 may be squeezed, and liquid therein may be pushed through tube 110 into the patient's mouth. Alternatively, a syringe such as one of syringes 304 may be coupled to the end of tube 110 to allow liquid to be dispersed into the patient's mouth.

The center portion of FIG. 3 illustrates another mechanism for dispersing liquid into the tube. The bottle 310 may include a pump mechanism to allow a patient or other user to push liquid into the tube and into the patient's mouth.

Further, an automatic pump 320 may be used to automatically control the flow rate of liquid pushing into the patient's mouth. This may enable a controlled flow of liquid to be dispersed into the patient's mouth during the course of a night or long procedure, to alleviate problems due to dry mouth.

It should be noted that although three types of devices for dispersal of fluids are illustrated, any other device suitable for causing fluids to be dispersed via the device described herein may be used.

Advantages of the disclosed systems and devices may include the ability to control a patient's mouth hydration without constant monitoring. Further, devices disclosed herein can allow water, medicine, nutrients, or other liquids to be dispersed directly to a patient's system, either quickly or over a long period of time.

In some examples, the disclosed device may be useful for an athlete. For instance, a competitive bike rider may be able to use this device to maintain hydration without the need to reach back and grab a conventional water bottle. The devices disclosed herein may allow constant hydration without the need for the user to touch or control anything with his or her hands.

Further, example devices can be used without hindering the user's speech, and can be used in conjunction with one or more other medical devices or apparatuses, including those which require the use of intubation tubes and/or mouth covering devices.

In addition, the mechanism for dispersing liquids directly to a patient's mouth may not rely on gravity, and as such the position of the patient (e.g., standing, sitting, lying down) may not impact the effectiveness of the device.

In some examples, the pump or other fluid dispersing mechanism may be configured to provide a particular flow rate, or VTBI (volume to be infused) over time. This flow rate may be set by a user and controlled based on the particular use of the device (e.g., recreational hydration, user during sleep, oral surgery, etc.).

In some examples, the device may include a humidity sensor configured to measure the humidity of a patient's mouth. This sensor may be used to provide feedback, and enable the user or a computing device to monitor and maintain a desired humidity level. This sensor may be coupled with the connector 130 shown in FIG. 3.

In further examples, the device may include a flow rate sensor, or other mechanism configured to measure a rate of dispersal of fluid into a patient's mouth. The device may provide feedback that can be used to control a pump or other fluid dispersing mechanism to maintain or change a rate of dispersal.

In some examples, the fluid source, pump, or other mechanism may bias fluid toward the inner mouth portion 132 of the device. The device may also include a valve or other fluid stopping mechanism (e.g., as a part of the connector 130), that can be activated by a user. In some examples, the user may bite down, causing the valve to open. In this case, when the user bites down, the fluid may be pushed into the inner mouth portion 132 and dispersed into the user's mouth.

In this application, the use of the disjunctive is intended to include the conjunctive. The use of definite or indefinite articles is not intended to indicate cardinality. In particular, a reference to "the" object or "a" and "an" object is intended to denote also one of a possible plurality of such objects. Further, the conjunction "or" may be used to convey features that are simultaneously present instead of mutually exclusive alternatives. In other words, the conjunction "or" should be understood to include "and/or". The terms "includes," "including," and "include" are inclusive and have the same scope as "comprises," "comprising," and "comprise" respectively.

The above-described embodiments, and particularly any "preferred" embodiments, are possible examples of implementations and merely set forth for a clear understanding of the principles of the invention. Many variations and modifications may be made to the above-described embodiment(s) without substantially departing from the spirit and principles of the techniques described herein. All modifications are intended to be included herein within the scope of this disclosure and protected by the following claims.

The invention claimed is:

1. A device for oral hydration, comprising:
 a flexible tube comprising a feeder line and a mouth portion connected together at a connection point,
  wherein the mouth portion of the flexible tube includes:
   a distal end that is looped around toward the connection point,
   a lower portion configured to conform to an exterior of lower gums of a patient's mouth,
   an upper portion configured to conform to an exterior of upper gums of the patient's mouth, and
   two opposing rear portions extending between and connecting the upper portion and the lower portion and positionable at a rear of the patient's mouth, and
  wherein the mouth portion of the flexible tube defines a plurality of holes positioned along a length of the mouth portion between the connection point and the distal end to enable liquid to be dispensed onto the exterior of the upper and lower gums of the patient's mouth; and
 a looped flexible cover configured to encapsulate the mouth portion of the flexible tube.

2. The device of claim 1, further comprising a connector coupled to the feeder line opposite the connection point and configured to fluidly connect the flexible tube to a fluid source.

3. The device of claim 1, wherein the mouth portion of the flexible tube defines the plurality of holes to be the same size as each other and evenly spaced along the length of the mouth portion.

4. The device of claim 1, wherein the looped flexible cover comprises cotton.

5. The device of claim 1, wherein the looped flexible cover comprises foam.

6. The device of claim 1, further comprising a pump configured to provide fluid to the flexible tube.

7. The device of claim 1, wherein the mouth portion of the flexible tube is configured to enable a flow rate of the liquid onto the exterior of the upper and lower gums of the patient's mouth, deform in response to a biting motion of the patient, and responsively modify the flow rate with deformation.

8. The device of claim 1, wherein the flexible tube is configured to maintain a position in the patient's mouth without contacting the patient's teeth.

9. The device of claim 1, wherein the plurality of holes defined by the mouth portion comprise a plurality of perforations.

10. The device of claim 1, wherein the mouth portion of the flexible tube defines the plurality of holes to be evenly spaced along the length of the mouth portion, wherein the plurality of holes includes a first hole positioned proximate to a proximal end of the mouth portion and a second hole positioned proximate the distal end of the mouth portion, and wherein the first hole is smaller than the second hole.

11. The device of claim 10, wherein a size of the plurality of holes follows a gradient, such that each of the plurality of holes positioned between the first hole and the second hole is progressively larger than an adjacent hole.

12. A device for oral hydration comprising:
 a flexible tube comprising a feeder line and an mouth portion connected together at a connection point,
  wherein the mouth portion of the flexible tube includes:
   a distal end that is looped around toward the connection point,
   a lower portion configured to conform to an exterior of lower gums of a patient's mouth,
   an upper portion configured to conform to an exterior of upper gums of the patient's mouth, and
   two opposing rear portions extending between and connecting the upper portion and the lower portion and positionable at a rear of the patient's mouth, and
  wherein mouth portion of the flexible tube is formed of a porous material that enables liquid to be dispensed onto the exterior of the upper and lower gums of the patient's mouth; and
 a looped flexible cover configured to encapsulate the mouth portion of the flexible tube.

13. The device of claim 12, further comprising a connector coupled to the feeder line opposite the connection point and configured to fluidly connect the flexible tube to a fluid source.

14. The device of claim 12, wherein the looped flexible cover comprises cotton.

15. The device of claim 12, wherein the looped flexible cover comprises foam.

16. The device of claim 12, further comprising a pump configured to provide fluid to the flexible tube.

17. The device of claim 12, wherein the mouth portion of the flexible tube is configured to enable a flow rate of liquid onto the exterior of the upper and lower gums of the patient's mouth, deform in response to a biting motion of the patient, and responsively modify the flow rate with deformation.

18. A device for oral hydration, comprising:
 a looped flexible cover; and
 a flexible tube comprising a feeder line and a mouth portion connected together at a connection point, wherein the mouth portion is encapsulated within the looped flexible cover and includes a distal end looped around within the looped flexible cover toward the connection point, wherein the mouth portion and the looped flexible cover are configured to conform to and extend along an exterior of lower and upper gums adjacent an oral vestibule of a user, and wherein the mouth portion defines a plurality of holes positioned along a length of the mouth portion between the connection point and the distal end to enable liquid to be supplied into the oral vestibule of the user.

19. The device of claim 18, wherein the looped flexible cover is formed of absorbent or semi-absorbent material to enable the liquid dispensed by the mouth portion of the flexible tube to be absorbed and slowly dispersed into the oral vestibule of the user over time.

20. The device of claim 18, wherein the mouth portion and the looped flexible cover are configured to extend along the exterior of lower and upper gums without contacting teeth of the user such that the teeth and jaw of the user are able to move freely without dislodging the flexible tube or the looped flexible cover.

\* \* \* \* \*